(12) United States Patent
Gaur

(10) Patent No.: US 11,688,068 B2
(45) Date of Patent: Jun. 27, 2023

(54) METHODS AND SYSTEMS FOR MONITORING SKIN RELATED METRICS

(71) Applicant: Girija Gaur, Arcadia, CA (US)

(72) Inventor: Girija Gaur, Arcadia, CA (US)

( * ) Notice: Subject to any disclaimer, the term of this patent is extended or adjusted under 35 U.S.C. 154(b) by 65 days.

(21) Appl. No.: 17/019,317

(22) Filed: Sep. 13, 2020

(65) Prior Publication Data
US 2022/0138948 A1 May 5, 2022

Related U.S. Application Data

(60) Provisional application No. 62/906,207, filed on Sep. 26, 2019.

(51) Int. Cl.
| | | |
|---|---|---|
| G06K 9/00 | (2022.01) | |
| G06T 7/00 | (2017.01) | |
| G16H 10/40 | (2018.01) | |
| G16H 30/40 | (2018.01) | |

(52) U.S. Cl.
CPC .......... G06T 7/0016 (2013.01); G16H 10/40 (2018.01); G16H 30/40 (2018.01); *G06T 2207/10064* (2013.01); *G06T 2207/30088* (2013.01); *G06T 2207/30201* (2013.01)

(58) Field of Classification Search
CPC . G06T 2207/30088; G06T 2207/30201; G06T 2207/30041; G06T 7/001; G06T 7/97; G06T 2207/20212–20224; G06T 7/0002–0016; G06T 2207/30108; G06T 2207/30128; G06T 2207/30168; A61B 5/44–447; A61B 5/4848; G06V 40/16; G06V 40/168–171; A61Q 1/00–14; A61Q 17/00–04; A61Q 19/00–10; A61K 8/00–14; G01N 33/5008–5017; G01N 2800/20–207; A45D 2044/007
See application file for complete search history.

(56) References Cited

U.S. PATENT DOCUMENTS

| | | | | |
|---|---|---|---|---|
| 2005/0220833 | A1* | 10/2005 | Slavtcheff | A61K 8/0208 |
| | | | | 424/401 |
| 2010/0271470 | A1* | 10/2010 | Stephan | A61B 5/442 |
| | | | | 382/164 |
| 2015/0177221 | A1* | 6/2015 | Peterson | A61K 8/92 |
| | | | | 356/402 |
| 2019/0035080 | A1* | 1/2019 | Bisker | G06T 7/75 |
| 2019/0059806 | A1* | 2/2019 | Shen | A61B 5/442 |
| 2019/0340774 | A1* | 11/2019 | Patwardhan | A61B 5/442 |
| 2020/0146622 | A1* | 5/2020 | Bock | G06T 7/0016 |
| 2021/0315512 | A1* | 10/2021 | Depfenhart | A61B 5/004 |

FOREIGN PATENT DOCUMENTS

| | | | | |
|---|---|---|---|---|
| WO | WO-2015097183 | A2 * | 7/2015 | A61B 5/1075 |

* cited by examiner

*Primary Examiner* — Atiba O Fitzpatrick

(57) ABSTRACT

Methods and systems for providing various skin-related metrics and tracking the effects of skincare and cosmetic products are described. The system may acquire user images via optical scanning methods and analyze the images before and after application of a product to provide quantitative feedback to the user of beneficial or adverse effects of the product. The system may track response of the skin based on changes in inflammation, dryness, elasticity, pH levels, and/or microbiomes and correlate these changes with user information including ethnicity, location, and lifestyle to generate models that are capable of predicting a user's response to certain ingredients and/or predicting long-term effects of certain ingredients on the skin.

8 Claims, 8 Drawing Sheets

METHODS AND SYSTEMS FOR MONITORING SKIN RELATED METRICS

CROSS-REFERENCE TO RELATED APPLICATIONS

This application claims the benefit of U.S. Provisional Patent Application No. 62/906,207 filed Sep. 26, 2019, which is incorporated by reference herein in its entirety.

BACKGROUND

With increasing exposure of people to various chemicals, a need exists to derive quantitative information associated with the effects of such chemicals on skin and surrounding tissue structures. Methods and systems are described for monitoring various skin-related metrics that may be associated with variations in blood flow, oxidative stress, inflammation, brightness, elasticity, moisture content, UV damage, and pigmentation. The system may identify the presence of external elements, such as chemicals, cosmetics, bacteria, and pollutants, and correlate the effects of such external elements with the response of skin and its surrounding tissue structure via optical interrogation techniques. Such systems address the need for analyzing the effects of increasing pollution levels, cosmetics, skincare formulations, lifestyle factors, user locations and microbiomes on overall user health.

SUMMARY

In light of the foregoing background, the following presents a simplified summary of the present disclosure in order to provide a basic understanding of some aspects described herein. This summary is not an extensive overview and is not intended to identify key or critical elements or to delineate the scope of the claims. The following summary merely presents various described aspects in a simplified form as a prelude to the more detailed description provided below.

Embodiments herein relate to a method of tracking skin response to exposure of chemicals and/or skincare formulations that a user is interested in testing. The method may acquire a sequence of user images, including sub-surface layers, at varying distances and/or light conditions, before application of a product and/or after application of the product. The changes in skin may be tracked based on variations in microbiome data and/or signs of inflammatory responses such as redness and/or swelling. In some embodiments, analysis of the sequence of images may provide insights into pH levels of the skin before and after application of the product.

The methods and systems may incorporate user information such as skincare routines, cosmetic applications, age, ethnicity, location, diet, lifestyle patterns, and/or other health metrics into analyzing the various skin-related metrics. Image processing, machine learning and artificial intelligence driven models can be applied to aggregated user information and skin-related metrics to provide user guidance on improving the skin-related metrics.

The summary here is not an exhaustive listing of the novel features described herein and is not limiting of the claims. These and other features are described in greater detail below.

BRIEF DESCRIPTION OF THE DRAWINGS

Embodiments are herein described, by way of example only, with reference to the accompanying drawings, wherein.

DETAILED DESCRIPTION

Figure 1:
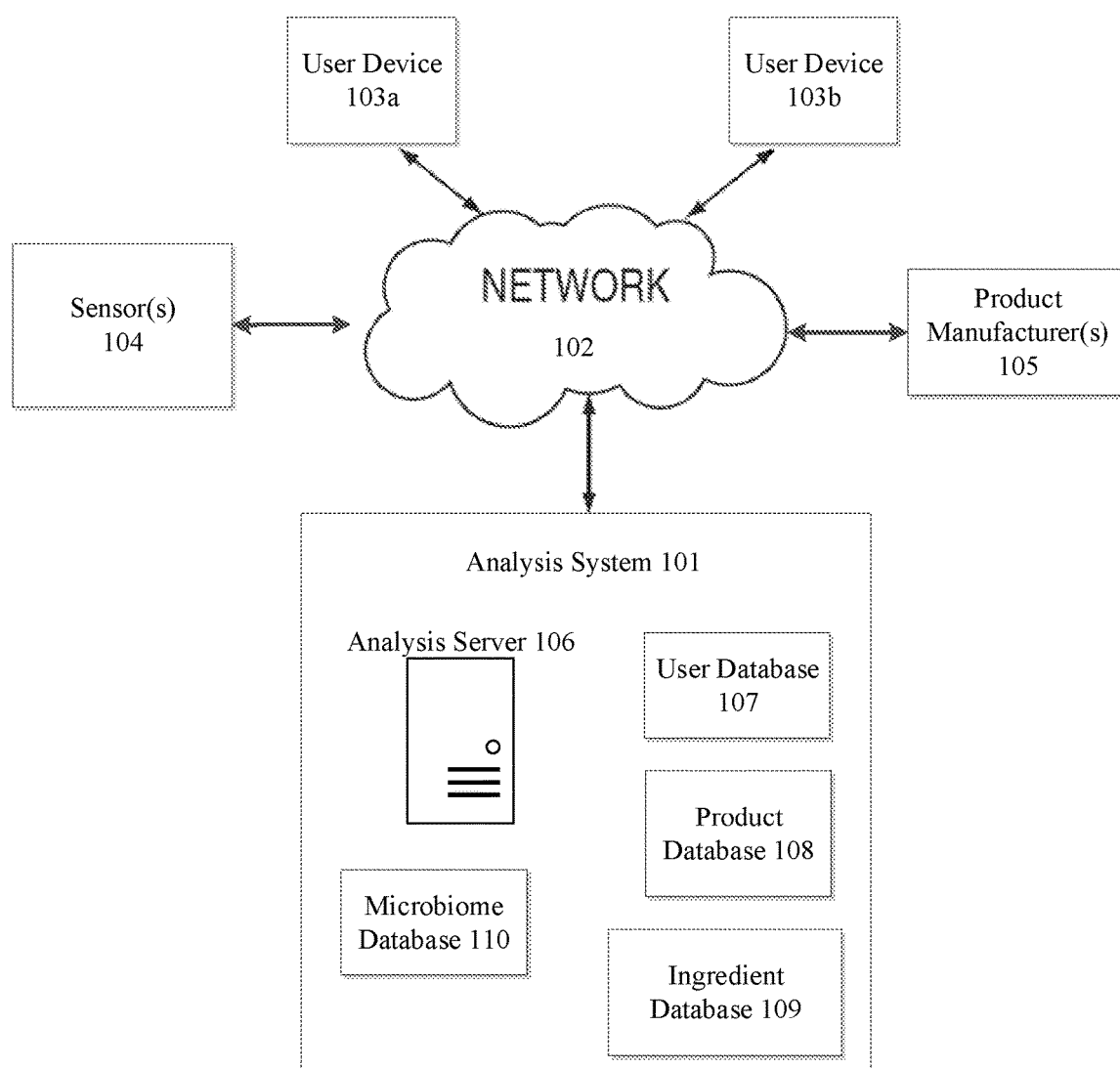
FIG. 1 shows an example illustration of the system in accordance with some aspects of the disclosure.

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure.

In describing various aspects, the same component on different drawings may be designated by the same reference numeral, and repetitive description of the same component will be omitted.

With the increasing use of new ingredients (e.g., herbal extracts, chemicals, nanoparticles, etc.) in cosmetics, skincare products, household products, fragrances, textiles, and other consumables that people may be exposed to, a need exists to extract information associated with the influence of such products on skin. A natural skin surface pH is generally close to 5. Application of various skincare products and/or cosmetics may alter the natural skin pH making it too basic or too acidic. Such alterations of skin pH may drastically affect skin flora, microbiomes, elasticity, moisture, and other skin related metrics. Moreover, there are thousands of products in markets currently with new products being released every day.

Currently, there are no methods to reliably monitor and quantify the effects of any of these products on skin on a personalized level in a convenient way (e.g., using a smartphone at home). Additionally, no methods exist to quantify and/or predict effects of a combination of such products on skin which may exacerbate skin related issues due to unknown interactions between multiple skincare products and skin.

Therefore, long term effects of such products need to be monitored including a method for estimating long term effects of the absorption of such products into the skin and in some cases, through the skin and into the bloodstream. without needing to make appointments with dermatologists and other skin care specialists. Such means would free-up significant amount of time, save costs for consumers as well as insurance providers, provide personalized tailored services and diagnostics that are currently lacking. It would provide consumers means to adjust skincare and/or cosmetic applications at their own convenience, improve skin health, their self-confidence, as well as avoid use of harmful chemicals that may get absorbed into bloodstreams and cause long term adverse health consequences that currently cannot be monitored. Methods and systems are described for monitoring applications of skincare products and cosmetics identifying, tracking, and/or analyzing skin microbiomes. The system may determine changes in skin pH levels following exposure to products and/or chemicals by analyzing variations in the skin microbiome. Big data analysis techniques may be used for tracking products on the market, release of new products, their respective ingredients, and adverse/beneficial effects corresponding to the individual ingredients and the respective products.

FIG. 1 shows an example illustration of the system 100 for identifying and monitoring skin related metrics. The system may include an analysis system 101, network 102, user devices 103a-b, and sensor(s) 104. The analysis system 101 may include various computational processors such as the analysis server 106 and databases such as user database 107, product database 108, ingredient/chemical impact database 109, and microbiome database 110. The various processors and/or servers may be configured to perform various functions including locating and retrieving user data, encrypting user communications, sending and receiving user data, directing image capture, image processing, data mining, and implementing machine learning and/or artificial intelligence algorithms.

Network 102 may be any type of information distribution network, such as satellite, telephone, cellular, wireless, optical fiber, coaxial cable, and/or a hybrid fiber/coax (HFC) distribution network. Additionally, network 102 may be a combination of networks. Network 102 may use a series of interconnected communication links (e.g., coaxial cables, optical fibers, wireless, etc.) and/or some other network to connect the analysis system 101 with the user devices 103a-b, sensor(s) 104, and/or a third-party device 105. The third-party device may be associated with a cloud storage or cloud computation platform.

The user devices 103a-b may be smartphones, tablets, drones, robotic assistants, etc. The sensor(s) 104 may include standalone devices (e.g., spectroscopes, cameras, microscopes, lidars, photodetectors, handheld imaging devices, hyperspectral imagers, etc.) that may connect to accessories for aiding image capture such as fiber optic probes, collimators, and lenses. The sensors may acquire imaging data associated with wavelengths varying between 400 nm to 1700 nm at spectral resolutions varying between 20 nm and 2 nm.

In some embodiments, the sensors may include at least one light source such as a tunable laser, LED and a broad-spectrum light source. In other embodiments, the light source may be independent of the sensor. The light source may be configured to illuminate an imaging area of interest. The sensors may include a computing device for acquiring, analyzing, and/or outputting data such as a computer, laptop, smartphone, tablet, cloud server, and an IoT device.

Figure 2:
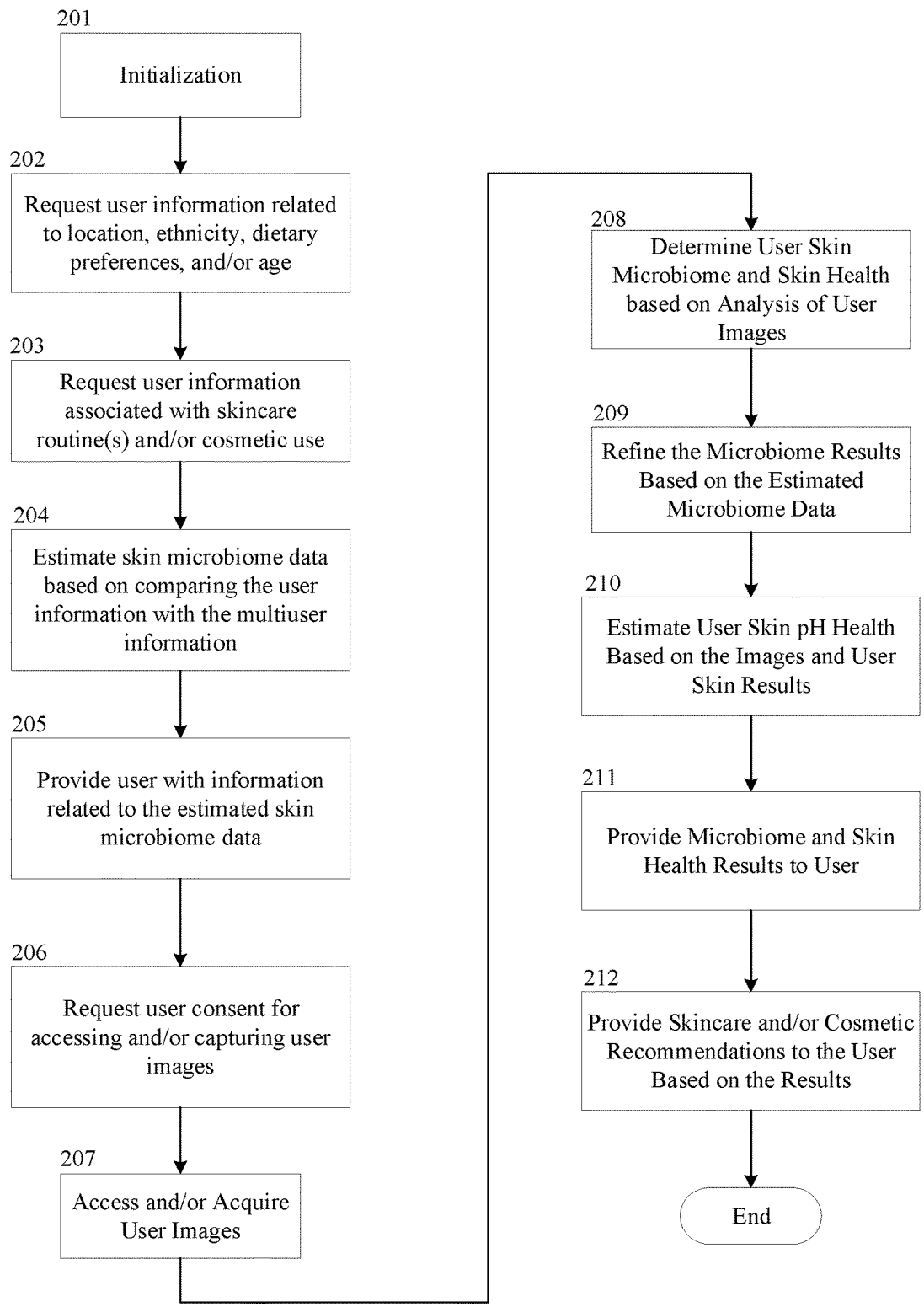
FIG. 2 shows a flow chart for a method of operating the system in accordance with some aspects of the disclosure.

FIG. 2 shows an exemplary flow chart for the skin analysis method in accordance with various aspects of the embodiments. Depending upon the results of the skin analysis, the system may further provide skincare and/or cosmetic recommendations. At 201 the system may begin initialization including setting up communication pathways with remote servers (e.g., the analysis server 106) and/or databases (e.g., user database 107, product database 108, chemical impact database 109, and microbiome database 110).

The system may request user information associated with ethnicity, location, dietary preferences, and/or age at 202. Such information may be used by the analysis system for determining influence of hereditary skin conditions, pollution levels at that location, age, and diet choices on various skin-related metrics and may comprise a first set of factors that influence the skin related metrics. Weighted influence associated with each factor of the first set of factors can then be determined by the system based on data mining and AI algorithms.

In some instances, the system may request information associated with user lifestyle such as exercise habits, job related activity metrics (e.g., desk, travel, lab work, exposure to hazardous materials, farming, hospital environment, etc.), smoking, alcohol consumption, cosmetic use, skincare use, etc. and may comprise a second set of factors that influence the skin-related metrics. Weighted influence associated with each factor of the second set of factors can then be determined by the system based on the AI algorithms. Increase in screen time related to work, sedentary lifestyles and other lifestyle choices may hamper healthy blood circulation and cause inadvertent other adverse effects on various skin-related metrics. Therefore, such aggregated information from multiple users can be helpful in identifying correlations between such choices and user health, and consequently, skin-related metrics.

Moreover, travel and/or environmental changes are likely to affect skin microbiomes, duration of sleep, stress, relaxation times and other lifestyle choices that in turn may alter various skin-related metrics (e.g., presence of acne, sensitivity, eczema, psoriasis, changes in blood circulation, oxygenation, dark circles, inflammatory responses, etc.). Accordingly, in various aspects of the embodiments, the system may collect information associated with the first and second set of metrics to determine their influence on skin.

At 203, the system may request user information related to skincare routines and/or cosmetic products used. Such product use information can be used to determine effects of the cosmetics and/or skincare formulations on skin and in some aspects, on a user's long-term health. This is because many chemicals present in cosmetics and skincare formulations may be absorbed through the skin and/or consumed via exposure to lips, and may be absorbed into the bloodstream. In some cases, the chemicals may build-up over time in the user's body. With the increase of new and untested chemicals, herbal extracts, and nanoparticles in skincare formulations and cosmetics, and no methods to reliably monitor and quantify the effects of any of these products on skin, there exists an urgent need for the system 100 described herein that can provide users with personalized information related to their skin, and in some aspects, their overall health, in a convenient way (e.g., using a smartphone at home).

Therefore, long term effects of such products need to be monitored including a method for estimating long term effects of the absorption of such products into the skin and in some cases, through the skin and into the bloodstream.

Additionally, no methods exist to quantify and/or predict effects of a combination of such products on the skin which tends to exacerbate skin related issues due to unknown interactions between multiple skincare products and the skin.

In some aspects, one or more of the databases 107-110 and/or analysis methods may be stored on the user device 103a-b locally and the skin analysis may be carried out locally to protect user privacy. In some embodiments, a combination of local analysis and remote analysis may be used depending upon user privacy settings and processing power of the user device 103a-b. According to some embodiments, the sensor(s) 104 may interface with computing devices to perform the analysis locally or communicate with the remote servers to perform some combination of local and remote analysis.

At 204, the system may analyze the first and second set of metrics and/or compare the user information with multiuser information received from other users. The system may estimate user microbiome data based on the analysis and comparison results. For example, the system may use ethnicity and location information for a user, to identify probabilities of certain bacterial distributions on skin. This may be based on an estimate of bacterial distributions for people of the same ethnicity that are living in similar environments and/or exposed to similar living conditions. The system may use such estimations to predict probabilities associated with skin bacterial populations. As another example, the system may determine a correlation between lifestyle choices including dietary habits and user microbiomes. In some aspects, the system may determine a correlation between skincare routines and/or cosmetics use and user microbiomes. The system may scrape various online sources of information to further refine the influence of the first and second set of metrics on user microbiomes to improve bacterial probability prediction accuracies. The system may present these predictions to the user via various interfaces and user devices at 205.

At 206, the system may request user consent for accessing and/or capturing user images. The system may include an application on the user device that can guide the user on capturing one or more images at specific proximities, magnifications, lighting conditions, and other image capture settings. The user images may include imaging of subsurface layers such as epidermis, dermis, hypodermis, connective tissues, blood vessels, nerves, hair follicles, and/or fat cells.

Upon receiving user consent, the system may access and/or capture the images at 207. Image capture may include determining whether baseline images associated with the user are stored in an accessible database. If there are no baseline images in the database, the system may generate a user indication to begin baseline image acquisition. The user indication may cause output of one or more messages displayed to user via a user interface of the system that instruct a user to proceed with baseline image acquisition. The system may suggest the use of cleansers prior to baseline image acquisition. If baseline images associated with the user of the system are stored in the accessible database, the system may load these baseline images for comparison with images acquired after a certain time duration and/or product application. The baseline images may comprise images of skin, facial features (e.g., eye shapes, eyebrow shapes, eyebrow color, eye color), and/or other identifiable features (e.g., moles, freckles, pigmentation spots, discoloration regions, wrinkles, acne, scar tissue, and stretch marks).

The system may analyze the baseline images to extract unique baseline patterns associated with facial features and/or skin conditions of the user. Artificial intelligence and/or image processing algorithms may be used to extract large data sets of such facial features and/or skin conditions from the baseline images. The large data sets may be processed to identify the unique baseline patterns. For example, if several images are acquired of under eye regions, the system may recognize these regions based on various image processing techniques that may rely on recognizing eye contours, spacing between under-eye fine lines, and/or under-eye skin elasticity estimation. The eye contours, spacing between under-eye fine lines, and/or under-eye skin elasticity may provide a unique signature identifying the user, and such unique signatures may be tracked over time to estimate effects of skin treatments, aging, cosmetics, sun exposure, build-up of chemical residues, uneven application of cosmetics and/or other products.

At 208, the system may estimate various skin-related metrics and identify certain bacterial distributions based on analyzing the user images. For example, certain bacteria may have specific autofluorescence signatures that can be identified. As another example, certain types of bacteria may generate proteins that can also result in protein specific autofluorescence signatures. In some cases, a resolution of the images may be sufficiently high to provide direct imaging of bacterial distributions. Further, direct imaging data along with autofluorescence signature can be combined to generate fairly accurate bacterial microbiome maps.

In some embodiments, wavelength and/or polarization information of light reflected off the user may be detected. Instruments such as spectrometers are readily available with much research being devoted to manufacturing miniaturized and cost-effective spectrometers that could be integrated into user devices such as mobile phones, cameras, laptops, AR/VR glasses, etc. Other detectors such as lidars may also provide high resolution information about skin-related metrics of the user.

In some embodiments, the analysis of the user images may be based on comparisons with the baseline images. Such comparisons may provide valuable data on effects of products that come into contact with skin. For example, the system may analyze the acquired images to identify unique patterns within the images, wherein the unique patterns may be used for recognizing particular facial features and/or skin conditions. The unique patterns can then be used to track changes in the facial features and/or skin conditions.

At 209, the identified bacterial distributions may then be compared with estimated microbiome information from step 204 to further refine the results. The system further be able to estimate skin pH values based on the types and distributions of bacteria identified in step 210 and/or based on various user information accessible to the system. For example, the system may estimate a pH level based on estimations of bacterial colonies in and around the epidermal skin layers.

In some embodiments, the system may analyze the outputs of pH sensing devices including strips and meters to provide a more accurate estimate of pH levels (e.g., based on color changes of the pH strips). Such pH sensing devices may also provide information related to products used by the user.

At 211 the system may provide the information related to the microbiome, skin-related metrics, and other product related parameters to the user. At 212 the system may provide skincare and/or cosmetic recommendations to the user based on this information and/or other user information. For example, if pH levels are determined to be unsuitable, the system may recommend products that are specifically designed to bring a user's skin pH to ideal levels. As another example, the system may provide recommendations of products that are suitable for being used in a single skincare regimen and/or avoiding the use of two or more product(s) in the same regimen.

In some embodiments, the system may allow a user to compare information about one or more products obtained via the system with information provided by the manufacturer or the retailer from where the product was purchased. For example, the system may simplify the user's ability to verify pH levels of various formulations (e.g., lotions, serums and creams). The system may also provide incentives for users to compare identified pH information with advertised product information so that various issues that may compromise product quality may be identified. For example, unsafe storage and/or transportation practices may cause degradation in product quality over time. This may undermine product quality and lead to disappointing customer experiences. The various embodiments described herein, open up avenues for ensuring the quality of products consumed. Users may receive various incentives including discount coupons, free samples, upgraded user tier status, award points, gift cards, and/or incentives for providing product related information.

Figure 3:
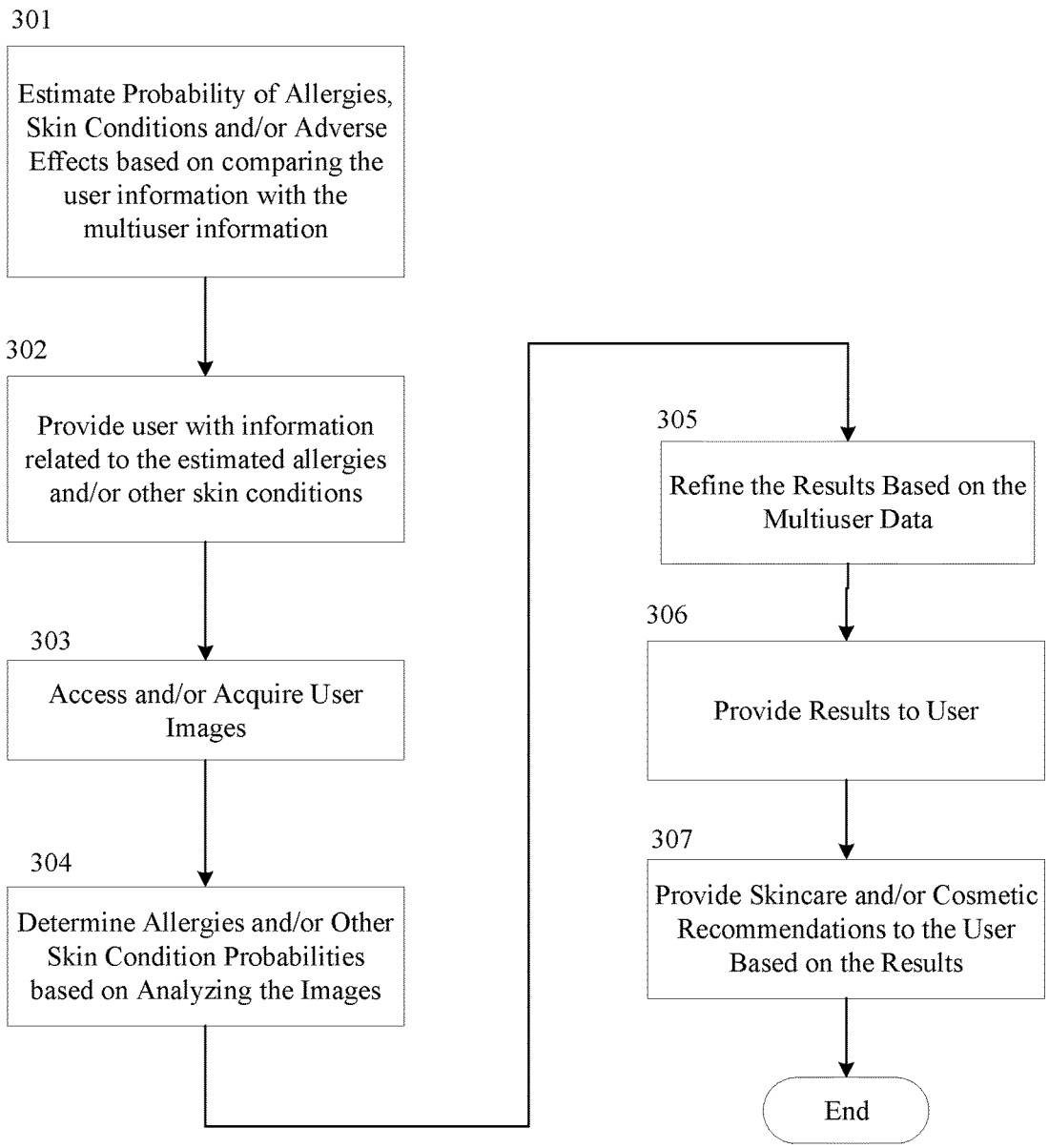
FIG. 3 shows a flow chart for a method of operating the system in accordance with some aspects of the disclosure.

FIG. 3 shows an exemplary flow chart for estimating potential allergic and/or adverse effects of certain chemicals and correlating these estimates with skincare and/or cosmetic recommendations. At 301, the system may analyze the user information associated with genetic databases, genealogy databases, ethnicity, location, age, lifestyles choices, educational attainments, etc. to estimate probabilities of adverse reactions to certain chemicals and/or herbal formulations found in the increasing number of skincare, cosmetic, and/or other household products including fragrances and incense sticks.

In some embodiments, the system may pool together and employ machine learning algorithms to identify probabilities of adverse effects of prolonged use of skincare, cosmetics, and/or other household products. For example, in many cases, users may not be allergic to certain ingredients and/or formulations but still suffer health risks upon continued and/or daily usage. In such situations, the system may monitor the effects of various products on users, compare the effects with known user profile information and determine correlations. The system may then present these correlations to the user so that the user may make a better-informed decision of whether to buy and/or use the product under question. With increasing skincare, cosmetic, and household products that keep on introducing new chemicals, fragrances, nanoparticles, and/or herbal formulations into the market, it is becoming increasingly difficult to vet the long-term safety associated with the use of these products.

An example of the lack of oversight and testing on long-term health effects of newly introduced and hyped products is the e-cigarette industry that over the course of a few years turned a major e-cigarette manufacturer into a multi-billion dollar company at the expense of the many lives of teens, young adults and their families by increasing nicotine dependence and exposing them to dangerous e-liquids whose effects on long-term inhalation were untested. Such oversight and rush to increase profits for startups combined with the consumption by teens and young adults of toxic chemicals, some potentially carcinogenic, led to fatal consequences. The immense toll of such untested products would have been mitigated if the e-liquid ingredients could have been At 302, the system may provide the probability estimates of adverse reactions to chemicals and/or products. In some embodiments, methods described herein are directed to improving the lives and safety of consumers by analyzing various products, tracking the effect of these products on users, and rapidly informing various users of potential adverse effects if any adverse reactions were detected in early users of those products.

At 303, the system may access and/or acquire user images as described earlier with respect to FIG. 2 and proceed to analyzing the images to determine whether the user has any existing skin conditions, allergic reactions, and/or may be exhibiting adverse reactions to one or more products the user has been exposed to at 304. Normalized images may be used to build a personalized analysis system for each user, tailored to corresponding skin tone, skin concerns and/or imaging conditions.

At 305, the system may further refine the results of step 304 based on comparing the user data with that for multiple users registered with the system. This comparison may allow the system to eliminate false positives and/or confirm true positives. User location data can be mapped to further refine environmental, pollution, temperature, humidity and/or sun exposure dependent personalized user results.

At 306, the system may provide the refined results to the user and may provide skincare, cosmetic and/or other product recommendations to the user at 307. For example, the system may determine that the user may respond more favorably to the use of certain products widely used and/or recommended by registered users of the same ethnicity. The system may then provide this information to the user, at 307, so that the user may consider switching to not only a more recommended product but a product that has been recommended based on the user's own information such as ethnicity, age, skin type, lifestyle choices, allergic reactions, preferences (e.g., fragrance free, hypoallergenic, products) etc. The system thus provides personalized recommendations based on analyzing multiuser information, product information, and user information.

Figure 4:
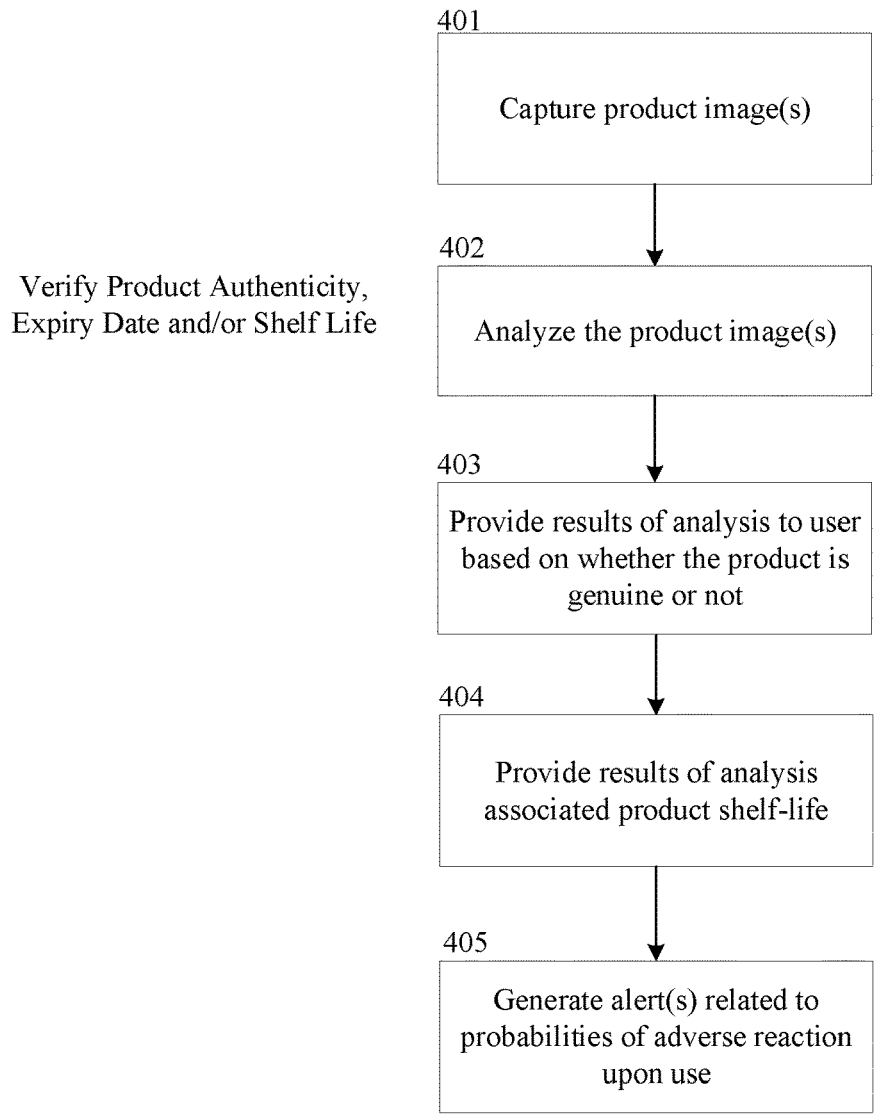
FIG. 4 shows a flow chart for a method of operating the system in accordance with some aspects of the disclosure.

FIG. 4 shows an exemplary flowchart for verifying authenticity of a product and estimating its shelf-life based on analyzing various aspects of product packaging and/or the formulation of the product. At 401, the system may capture one or more product images. The images may correspond to various product-specific packaging details (e.g., barcodes, manufacturer codes, seals, etc.) and/or correspond to the skincare or other formulation contained in the product package. The system may provide the user with a customized examination pod in which the formulation may be added.

At 402, the system may analyze the captured product images. In some embodiments, the examination pod may be configured to provide a baseline subtracted image of the formulation under test. For example, the examination pod may be black with a predetermined reflective surface that is configured to reflect incident wavelengths of light that pass through the formulation. The system may analyze the reflected light and/or apply other spectroscopic techniques to enumerate one or more metrics related to absorbance, reflectivity, color, and viscosity. These metrics may then be compared to those corresponding to an authentic product that may be provided directly by the manufacturer and/or based on testing products bought directly from the manufacturer. The wavelengths analyzed may vary between the visible and the infrared (e.g., 400 nm to 1700 nm).

At 403, the system may provide the results of the product test to the user. The results may include information pertaining to whether the product is genuine or not, and/or whether there may be signs of tamper. At 404, the system may provide an estimate of the shelf-life of the product. The estimated shelf-life may be based on information provided by the manufacturer in addition to the information obtained based on analyzing the formulation.

At 405, the system may generate an alert if any adverse effects of product use are suspected. For example, by analyzing the ingredients and formulation metrics as described at 402, the system may determine that continued product use could have adverse consequences on skin cells and one or more scores may be assigned to each of the products based on the adverse and/or beneficial effects. Determination of the effects may be based on determining that the ingredients of the product may be carcinogenic, exhibit cell toxicity upon accumulation, exhibit deep absorption through skin, and/or may be a counterfeit. The system can thus prevent the use of unsafe products.

In some embodiments, the system may track use of banned chemicals in products and consequently generate and send alerts to the FDA, users, inspection facilities, etc. blacklist unsafe vendors, and/or help spread public awareness. By mapping location data with tracked results of counterfeit and/or unsafe products, a real-time supply-chain network of such products can be identified and disrupted and increase the knowledge of day-to-day users.

In some embodiments, the system may track consumer interest in product type and/or usage of a particular product. The system may then provide registered users with periodic reports of changes in the one or more scores assigned to each of the products. The users may be offered incentives for providing feedback regarding the products used, such as skin reactions, changes in pH levels, changes in skin flora, reduced eczema, etc. The incentives may include promotional codes, discount codes for the products offered from sellers of those products. The feedback may be collected and analyzed using big data analytics and artificial intelligence to predict effects of the products on a diverse set of users on the basis of skin type, living location, ethnicity, lifestyle, age, gender, biorhythms, skin diseases, skin allergies, bacterial populations, and/or seasons. By collecting such data, the registered users may be provided a personalized recommendation that advises continued use of one or more products and/or provides an estimate of when skin pH levels might return to desirable levels after use of a specific product.

Figure 5:
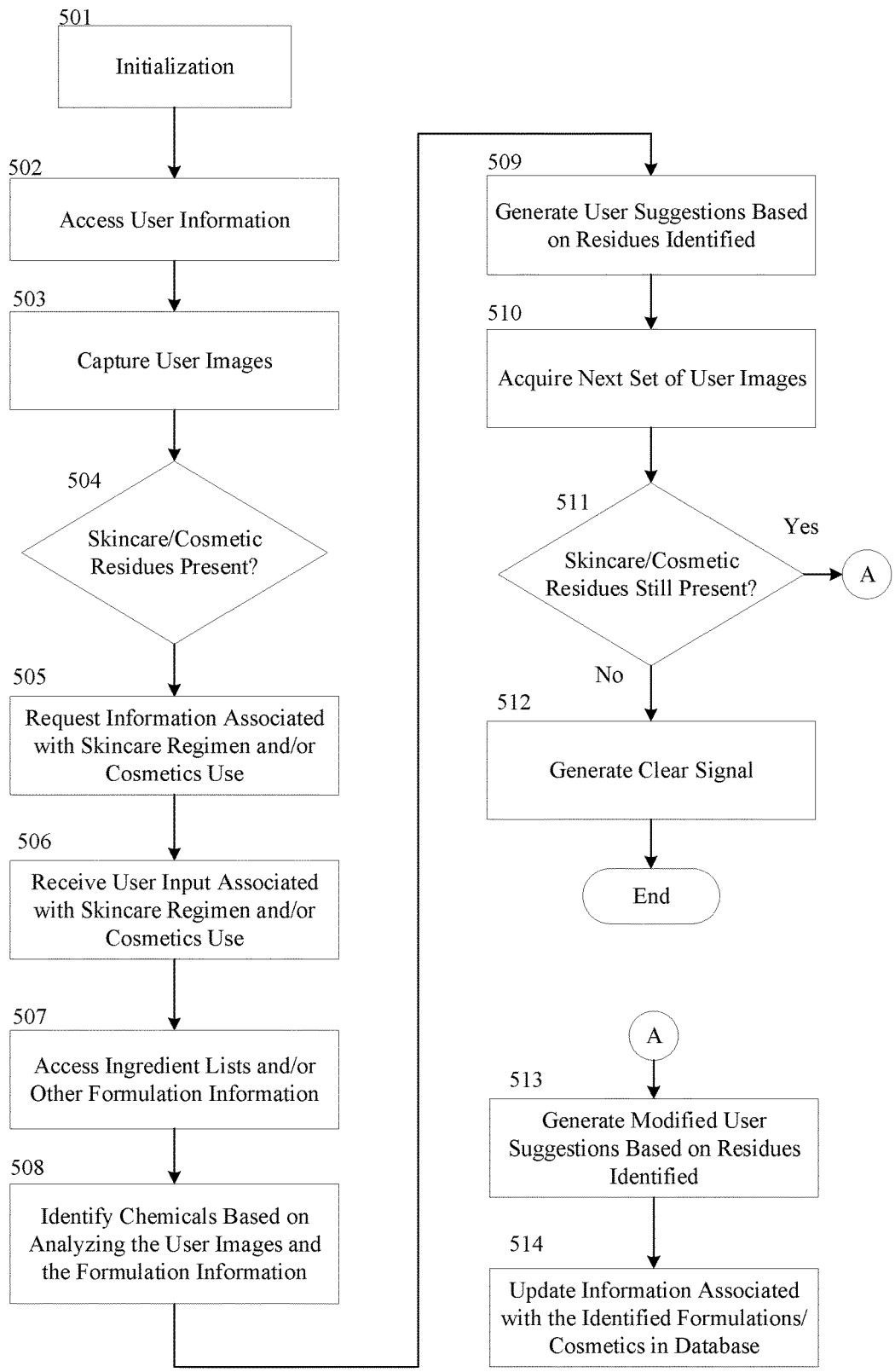
FIG. 5 shows a flow chart for a method of operating the system in accordance with some aspects of the disclosure.

FIG. 5 shows an exemplary illustration of a flow chart for determining efficacy of a user's cleansing routine. At 501, the system may initialize and establish communication channels with the user device, sensor, databases, and servers. At 502, the system may access user information associated with age, ethnicity, lifestyle, gender, location, skincare routines, cosmetic use, etc. as described earlier with respect to FIG. 2.

At 503, the system may capture one or more user images as described earlier with respect0 to FIGS. 2-4. The images may be calibrated to account for the variations in imaging distance, focus, optical setup, lighting conditions, and/or ambient environmental variations, such as temperature, humidity, and elevation. The sequence of images may include images taken after cleansing skin.

The system may analyze the user images to determine whether skincare and/or cosmetic residues are present at 504. Identification of the residues may be based on identifying facial color variations, irregularities of skin and/or facial hair, changes in reflection and/or absorption intensities, and sub-surface skin analysis. In some embodiments, detection of any residues may be achieved in real-time while image scans are being taken. If any residues are identified, Yes at 504, the system may generate an alert and/or request information pertaining to the user's most recent skincare regimen and/or cosmetic use at 505. The alert can serve to notify the user of areas of skin requiring additional cleansing and/or rinsing steps. The alert may comprise an audio, visual, audio-visual, and/or vibration alert. If no residues are present, No at 504, the system may proceed to 512 and generate a clear signal that is indicative of an effective cleansing routine.

At 506, the system may receive user input associated with the most recent use of skin-related products including household cleaners. At 507, the system may determine ingredients and/or formulation details associated with those products based on publicly available information, scarping internet sources of information and/or from manufacturers.

At 508, the system may identify products associated with the detected residues based on analyzing the images and the ingredients. The identification of the residues may be based on analyzing wavelength related information associated with the images. At 509, the system may inform the user of the residues and/or provide user suggestions for removal of the residues. For example, if the system determines that some traces of eyeliner are present, the system may inform the user of the presence and approximate location of the eyeliner residue.

At 510, the system may acquire a next set of user images once the user has confirmed that another cleansing step was performed.

At 511, the system may analyze the next set of user images to determine whether the residues are still present. If no residues are detected the system may proceed to 512 and generate a "clear" signal indicative of successful cleansing. If residues are still detected, the system may proceed to 513 and generate modified user suggestions. For example, the system may recommend cleansers that exhibit higher cleansing efficacy associated with the identified eye liner residue.

At 514, the system may update various product, user, and/or ingredient databases based on the skincare and cosmetic products used and the residues identified. The system may collect such information from multiple users and refine the user suggestions based on analyzing this information obtained from multiple users.

In some embodiments, the system may determine various skin-related metrics after analyzing the first and second set of user images such as dryness, elasticity, wrinkles, pH levels, microbiome distributions, and moisture content. The information related to the skin-related metrics may then be correlated with the cleansing products used and the results of the correlation stored in the product, ingredient and/or user databases.

Figure 6:
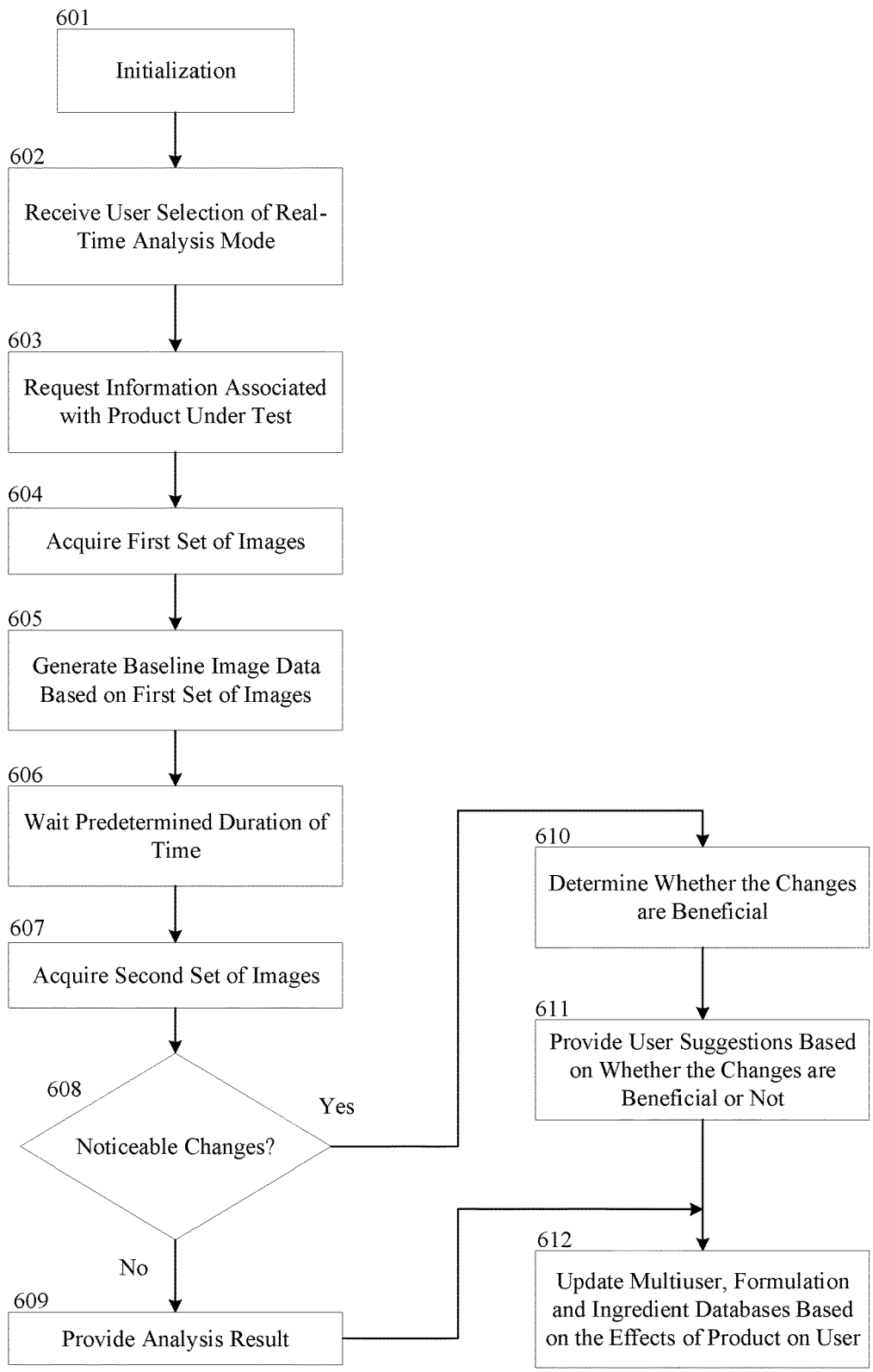
FIG. 6 shows a flow chart for a method of operating the system in accordance with some aspects of the disclosure.

FIG. 6 shows an exemplary flowchart for tracking effects of a new product on skin. Currently, in order to test the effects of a new product on skin, users need to apply a small amount and then wait for an entire day before determining that no adverse reactions are seen. In some cases, the adverse reactions may escape the user's examination because of being limited to a very small area and being noticeable only upon magnification. The systems and methods described herein require users to wait for only a few minutes before providing quantitative information associated with application of the new product. For example, the user may apply the product for only 5 minutes before the system scans the area of application and provides information pertaining to any adverse reactions such as increased redness, inflammation, variations in surface pH, and/or microbiome changes.

At step 601, the system may initialize as described earlier with respect to FIG. 5. At 602, the system may receive user indication of analyzing product effects on skin in a real-time analysis mode. For example, the user may want to test the effects of a new skincare product and determine whether any adverse reactions occur before leaving the home. The system may then request the user to provide information associated with the product under test at 603. The information may include brand name, product name, a product category, and/or user desired effect of the product.

At 604, the system may acquire images for generating baseline images at 605 before application of the product under test. The images may include those taken after cleansing skin or after application of skincare/cosmetic products.

Image acquisition may be similar to that described earlier with respect to FIGS. 1-5. For example, the images may be calibrated to account for the variations in the imaging distance, focus, optical setup, lighting conditions, and/or ambient environmental variations, such as temperature, humidity, and elevation.

The system may wait for a predetermined duration of time during which the user can apply the product being tested at 606. In some embodiments, the system may wait for a user input that is indicative of having applied the product.

At 607, the system may proceed with acquiring images after application of the product being tested. If any noticeable changes are present, Yes at 608, the system may proceed to analyzing the changes at 610. If no noticeable changes are detected, No at 608, the system may proceed to 609 and inform the user that no adverse effects have been detected.

At 610, the system may analyze the changes and determine whether they are beneficial or not. For example, some products that target acne or inflammation may exhibit calming effects within a few minutes of application. In some aspects, the calming effects may be determined based on changes in spectral information. For example, inflammation tends to be accompanied by increased blood flow to the affected regions. In some instances, this may be accompanied by an increase in temperature. Optical imaging techniques that rely on infrared and/or near-infrared wavelengths can be capable of resolving blood flow changes and/or temperature fluctuations. The system may then inform the user at 611 that the product is working as desired and that increased application of the product may be beneficial.

At 612, the system may update the multiuser, product and/or ingredient databases based on the effects of the product determined at 610. The information stored in the databases may then help the system improve the accuracy of predicting user responses to certain products and/or providing the user of skin related forecasts that may predict changes over certain durations of time (e.g., a week, a month, or a year).

Figure 7:
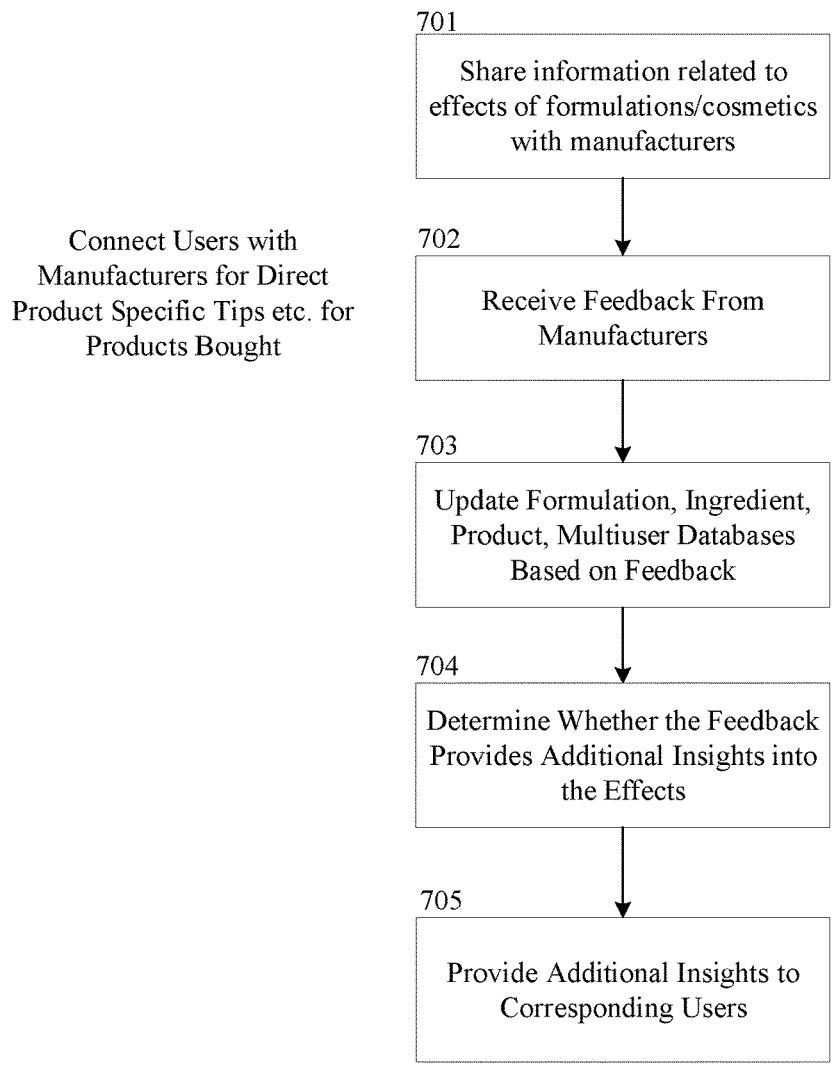
FIG. 7 shows a flow chart for a method of operating the system in accordance with some aspects of the disclosure.

FIG. 7 shows an exemplary illustration of a flowchart for connecting users with manufacturers of various skin related products. At 701, the system may share anonymous user reactions and/or feedback associated with certain products with the manufacturer so that the manufacturer may be better able to track user sentiments, user interest, and efficacy of their products. At 702, the system may receive feedback from the manufacturer related to the product and its expected effect. For example, the manufacturer may provide clinical data that provides quantitative data associated with test results of the product on a certain type of population. The manufacturer may also provide information pertaining to improvements being designed to the product formulation.

At 703, the system may update the databases associated with the product and ingredients based on the multiuser feedback and manufacturer feedback. At 704, the system may analyze the aggregated feedback information to determine whether any additional insights can be extracted. For example, the clinical test data may provide data associated with proven beneficial results for Asian women older than 40. This information may be used by the system to inform users that the product may be more effective for those who are ethnically Asian women, and over 40 at 705. As another example, the clinical data may be associated with an ethnically diverse population and showed greater product efficacy for long term use for those who started using the product at an early age (such as late twenties). The system may then provide this insight to registered users so that users who are older may benefit from other products that are more suitable for their age.

Figure 8:
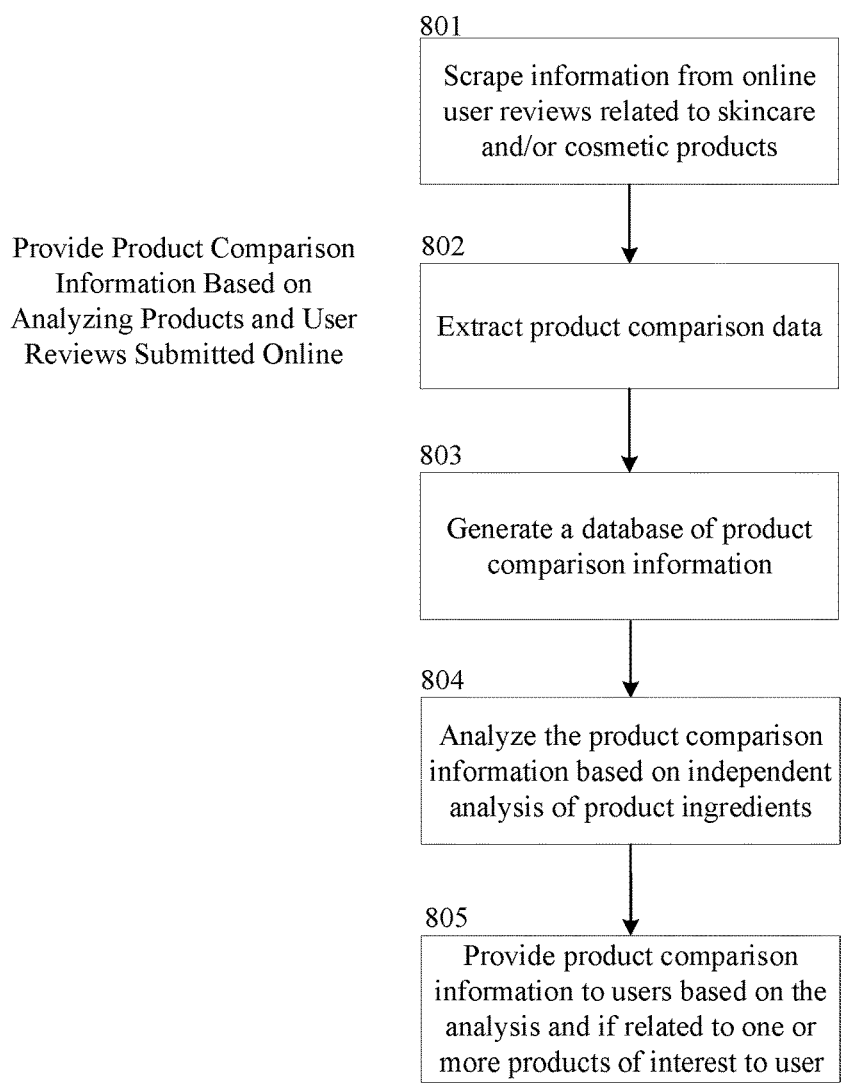
FIG. 8 shows a flow chart for a method of operating the system in accordance with some aspects of the disclosure.

FIG. 8 shows an exemplary flowchart for determining product comparisons from various external and/or internal sources of information and presenting these comparisons to the user. At 801, the system may scrape information from various online sources (e.g., social media posts, cached content, and manufacturer generated content) and internal sources including internally generated databases that track product ingredient benefits, adverse reactions, safety, and efficacy. At 802, the system may extract product comparison information from online sources. For example, in some cases, user reviews include information about other similar products that provided greater benefit than the product being reviewed. The system may identify such product comparisons and store the comparison data in a database at 803.

At 804, the system may analyze the product comparison data, ingredients, and reviews of the product scraped from the online sources to generate a product rating. The rating may take into account safety of all the ingredients of the product and/or may include an additional metric that informs the user of the safety of the ingredients. In some embodiments, the system may provide insights into the use of the product by multiple users and correlate similarities in multi-user information with skin response. Accordingly, the system provides a comprehensive method of tracking user feedback, experiences, interests, suggestions vis-à-vis other products and providing insights extracted from the aggregated multi-user information to the user.

While various embodiments described herein relate to optical interrogation methods, the systems and methods described herein may be applied to other forms of interrogation (e.g., sweat analyzers, breath analyzers, electrical probes and/or implants, ultrasound imaging and/or magnetic imaging) that provide the required and/or relevant information associated with at least products applied, effects of the products on the human body, verifying authenticity of the products, and identifying expiry of the product formulations.

While illustrative systems and methods as described herein embodying various aspects of the present disclosure are shown, it will be understood by those skilled in the art, that the invention is not limited to these embodiments. Modifications may be made by those skilled in the art, particularly in light of the foregoing teachings. For example, each of the elements of the aforementioned embodiments may be utilized alone or in combination or subcombination with elements of the other embodiments. It will also be appreciated and understood that modifications may be made without departing from the true spirit and scope of the present disclosure. The description is thus to be regarded as illustrative instead of restrictive on the present invention.

The invention claimed is:

1. A method comprising:
receiving, by an imager and from a user of the imager, information indicative of product under test including product name and product category;
receiving, by the imager and from the user, user input indicative of selection of real-time analysis mode;
acquiring, by the imager and at a start time of the real-time analysis mode, a first set of facial images of the user before facial application of the product under test;
acquiring, by the imager and at an end time of the real-time analysis mode, a second set of facial images of the user after facial application of the product under test, wherein the end time is a few minutes after the start time;

extracting a plurality of facial metrics of the user based on comparing the first set and the second set of facial images, wherein the plurality of facial health metrics is associated with two or more of inflammation, redness, and blood flow; and causing dispplay of a user suggestion associated with continued use of the product under test based on analyzing the plurality of facial health metrics.

2. The method of claim 1, wherein the causing the display of the user suggestion further comprises:

determining increased inflammation, redness, or blood flow for an imaged region associated with the first set and the second set of facial images; and generating user output indicative of worsening skin health for the imaged region.

3. The method of claim 2, further comprising:

updating a multiuser database based on the user output of the product under test.

4. The method of claim 1, wherein the generating the results is further based on user information provided by the user, the user information comprising one or more of the user's skincare routine, alcohol consumption, smoking habits, and sedentary habits.

5. The method of claim 4, further comprising:

updating an ingredients and product database based on the displayed user suggestion of the product under test.

6. The method of claim 1, wherein the acquiring the first and second set of facial images is based on optical imaging techniques.

7. The method of claim 1, wherein the causing the display of the user suggestion further comprises:

determining decreased inflammation, redness, or blood flow for an imaged region associated with the first set and the second set of facial images; and generating user output indicative of improved skin health for the imaged region.

8. The method of claim 2, further comprising:

causing display of a user alert indicative of harmful facial effects of the product under test.

* * * * *